US00PP25875P2

(12) United States Plant Patent
Ault

(10) Patent No.: US PP25,875 P2
(45) Date of Patent: Sep. 8, 2015

(54) *BAPTISIA* PLANT NAMED 'LUNAR ECLIPSE'

(50) Latin Name: ***Baptisia* hybrid**
Varietal Denomination: Lunar Eclipse

(71) Applicant: James Robert Ault, Libertyville, IL (US)

(72) Inventor: James Robert Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 72 days.

(21) Appl. No.: 13/999,432

(22) Filed: Feb. 25, 2014

(51) Int. Cl.
*A01H 5/00* (2006.01)

(52) U.S. Cl.
USPC ..... Plt./263.1

(58) Field of Classification Search
USPC ..... Plt./263.1, 226
See application file for complete search history.

*Primary Examiner* — Annette Para
(74) *Attorney, Agent, or Firm* — Penny J. Aguirre

(57) ABSTRACT

A new cultivar of hybrid *Baptisia,* 'Lunar Eclipse', that is characterized by its racemes of flowers that are light cream to light yellow in color at anthesis aging to a medium to dark violet-blue color, its flowers that are radially and uniformly dispersed around the racemes, its strongly vase-shaped, open habit with stems that are upright to slightly leaning, its mid to late bloom season; flowering for three weeks from late-May to mid-June in northern Illinois, its inflorescences that are borne above the foliage, and its lack of foliage on the bottom third of the plant exposing the lower stems.

2 Drawing Sheets

Botanical classification: *Baptisia* hybrid.
Cultivar designation: 'Lunar Eclipse'.

BACKGROUND OF THE INVENTION

The present invention relates to a new and distinct cultivar of hybrid *Baptisia* plant, botanically known as *Baptisia* 'Lunar Eclipse' and will be referred to hereafter by its cultivar name, 'Lunar Eclipse'. The new cultivar represents a new false indigo, an herbaceous perennial grown for landscape use.

The new invention arose from an ongoing breeding program in a dedicated test plot in Glencoe, Ill. The objective of the breeding program is to develop novel interspecific hybrids of *Baptisia* that exhibit unique flower coloration, hybrid vigor, ease of clonal propagation, and desirable plant habits.

'Lunar Eclipse' was selected as a single unique plant by the Inventor in June of 2009 after evaluating seedlings that derived from a cross made in June of 2003 between *Baptisia* 'Midnight' (U.S. Plant Pat. No. 20,432) as the female parent and an unnamed hybrid plant derived from open pollination of an interspecific hybrid *Baptisia* (*australis*×*sphaerocarpa*) from the Inventor's breeding program as the male parent.

Asexual propagation of the new cultivar was first accomplished by rooting of stem tip cuttings under the direction of the Inventor in July of 2009 in Glencoe, Ill. Asexual propagation by rooting of stem shoot tip cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Lunar Eclipse' as a unique cultivar of *Baptisia.*

1. 'Lunar Eclipse' exhibits racemes of flowers that are light cream to light yellow in color at anthesis aging to a medium to dark violet-blue color. This dramatic color transition is unique from *Baptisia* cultivars known to the Inventor.
2. 'Lunar Eclipse' exhibits flowers that are radially and uniformly dispersed around the racemes.
3. 'Lunar Eclipse' exhibits a strongly vase-shaped, open habit with stems that are upright to slightly leaning.
4. 'Lunar Eclipse' exhibits a mid to late bloom season, flowering for three weeks from late-May to mid-June in northern Illinois.
5. 'Lunar Eclipse' exhibits inflorescences that are borne above the foliage.
6. 'Lunar Eclipse' exhibits a lack of foliage on the bottom third of the plant, exposing the lower stems.

The female parent of 'Lunar Eclipse', 'Midnight', differs from 'Lunar Eclipse' in having inflorescences that are longer in length (an average of 68 cm), in having flowers that are persistently violet-blue in color, in having flowers that are smaller in diameter, and in having an earlier and longer bloom period. The male parent differs from 'Lunar Eclipse' in having flowers that are persistently blue-violet in color, in having an earlier bloom period, and in having inflorescences that are shorter in length (an average of 30 cm). 'Lunar Eclipse' can also be compared to typical plants of *Baptisia bracteata* (syn. *B. leucophaea*) and the *Baptisia*×*bicolor* cultivar 'Starlite' (U.S. Plant Pat. No. 19,971). Typical plants of *Baptisia bracteata* are similar to 'Lunar Eclipse' in having inflorescences that are borne above the foliage. Typical plants of *Baptisia bracteata* differ from 'Lunar Eclipse' in having flowers that are persistently cream to lemon yellow in color, in having horizontal inflorescences, in having flowers that are produced on only one side of the inflorescences, and in having an earlier bloom season. 'Starlite' is similar to 'Lunar Eclipse' in having flowers that are similar in size and in having flowers that are radially and uniformly dispersed around the raceme. 'Starlite' differs from 'Lunar Eclipse' in having flowers that are lavender and blue in color with a yellow keel, in having an earlier bloom season, in being more densely branched, and in being taller (an average of 100 cm) and wider (an average of 1.5 m) in overall plant size.

BRIEF DESCRIPTION OF THE DRAWINGS

The accompanying colored photographs illustrate the overall appearance and distinct characteristics of the new *Baptisia*. The photographs were taken in May of five year-old plants (FIG. 1), in June of four year-old plants (FIG. 2) and in July of six year-old plants (FIG. 3) as grown outdoors in a trial plot in Glencoe, Ill.

The photograph in FIG. 1 provides a close-up view of inflorescences of 'Lunar Eclipse'.

Figure 1:
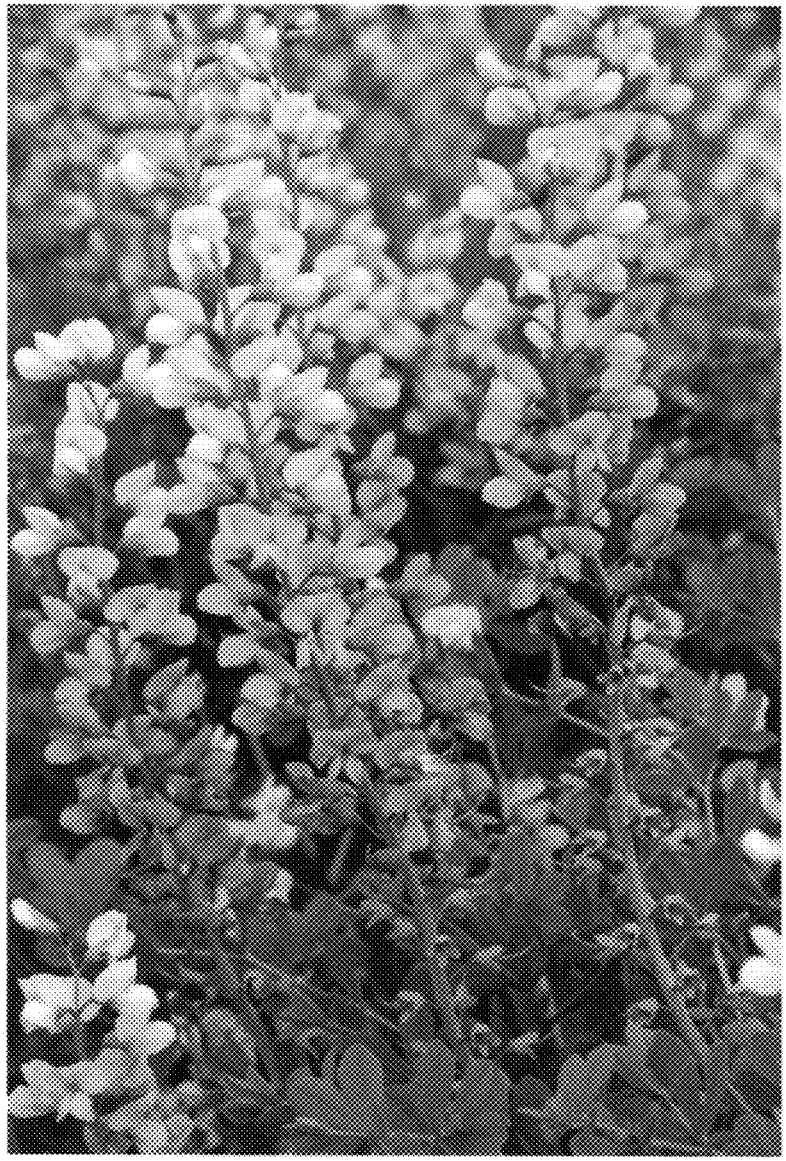
Figure 2:
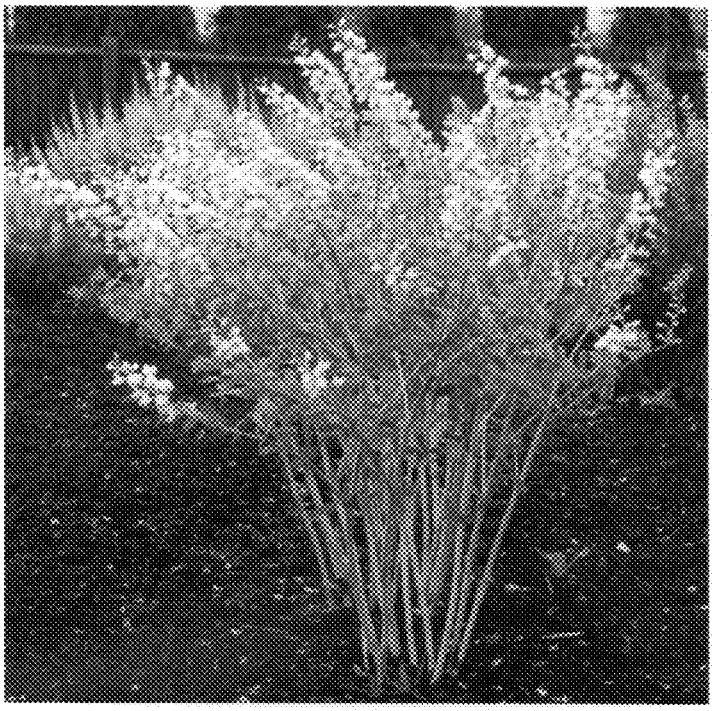

The photograph in FIG. 2 provides a side view of plants of 'Lunar Eclipse' in bloom illustrating the overall plant and flowering habit.

Figure 3:
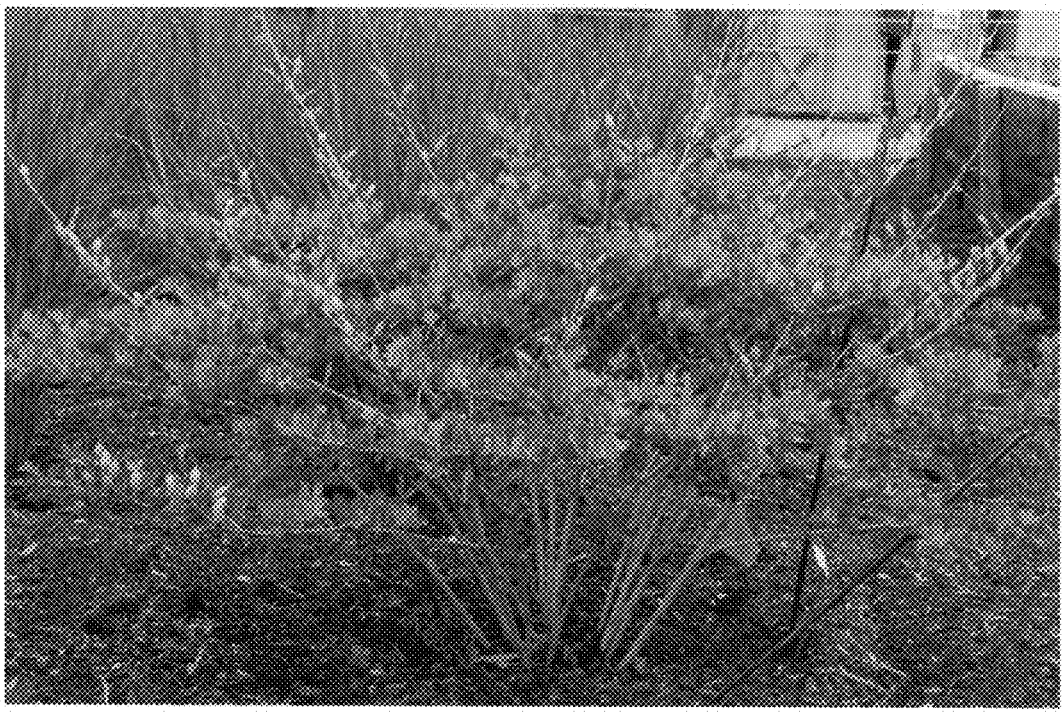

The photograph in FIG. 3 provides a side view of a plant of 'Lunar Eclipse' after bloom.

The colors in the photographs are as close as possible with the photographic and printing technology utilized and the color values cited in the detailed botanical description accurately describe the colors of the new *Baptisia*.

DETAILED BOTANICAL DESCRIPTION OF THE PLANT

The following is a detailed description of five year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Three weeks from late-May to mid-June in northern Illinois.

*Plant habit*.—Strongly vase-shaped, open habit.

*Height and spread*.—Up to 89 cm in height and 1 m in width.

*Hardiness*.—U.S.D.A. Zones 4 to 8.

*Diseases and pests*.—No susceptibility to diseases or pests has been observed.

*Root description*.—Deep rooted, fibrous.

*Propagation*.—Rooting of stem tip cuttings.

*Growth rate*.—Moderate.

Stem description:

*Branch habit*.—Moderately branched; average of 11 main branches with an average of 3 secondary branches and 1 to 2 tertiary branches per secondary branch.

*Stem size*.—Main stem; average of 90 cm (including peduncle) in length and 7 mm in width, secondary; average of 30 cm in length and 3 mm in width, tertiary; an average of 11 cm in length and 2 mm in width.

*Stem shape*.—Oval.

*Stem color*.—138B.

*Stem surface*.—Glabrous, glaucous and slightly satiny with ridges.

Foliage description:

*Leaf shape*.—Fan-shaped in overall outline.

*Leaf division*.—3-palmate.

*Leaf internode*.—Foliage begins 25 cm from base, an average of 10 cm on main stem and an average of 5 cm on secondary branches.

*Leaf size*.—Average 5 cm in length and 8 cm in width when mature.

*Leaf quantity*.—About 22 per stem.

*Leaflet shape*.—Oblanceolate.

*Leaflet base*.—Cuneate.

*Leaflet apex*.—Acute.

*Leaflet venation*.—Pinnate pattern, not conspicuous, color matches leaflet color on the upper and lower surface with the mid rib of lower surface 138B.

*Leaflet margins*.—Entire.

*Leaf attachment*.—Petiolate.

*Leaf arrangement*.—Alternate.

*Leaflet surface*.—Glabrous and slightly glaucous on upper and lower surface.

*Leaflet color*.—Newly expanded and mature upper and lower surface 137A.

*Leaflet size*.—An average of 5 cm in length and 1.9 cm in width.

*Petioles*.—Average of 7 mm in length and 2 mm in width, clasping to stem at mature nodes, 144B in color, surface is glabrous and satiny.

*Stipules*.—2 at leaf nodes, lanceolate to broadly lanceolate in shape, base is truncate to stem, apex is acute, up to 4 cm in length and 2 cm in width on mature leaves, 137A in color on upper and lower surface, glabrous and slightly glaucous on upper and lower surface.

Flower description:

*Inflorescence type*.—Terminal racemes of pea-like flowers on main and secondary branches, blooms from the base to the apex, flowers that are radially and uniformly dispersed around the racemes.

*Inflorescence size*.—Average of 38 cm in length and 5 cm in width.

*Lastingness of inflorescence*.—An average of 21 days.

*Flower size*.—An average of 2.5 cm in depth and about 2.3 cm in diameter.

*Flower fragrance* .—Faint.

*Flower number per inflorescence*.—An average of 42.

*Peduncle*.—Oval in shape, up to 40 cm in length and an average of 4 mm in width, a blend of 138B and 137C in color, surface is glabrous, satiny and slightly glaucous with ridges, flower internode length averages 1.5 cm.

*Petiole*.—About 6 mm in length and 1 mm in width, oval in shape, 138B and suffused with 200A in color, glabrous and satiny surface.

*Flower buds*.—Kidney-shaped, about 2.4 cm in length and 1.5 cm in width, petal portion is 155A in color and changing to a blend of 84D and 155A before opening, calyx portion same as open flowers.

*Flower type*.—Papilionaceous, held at about a 45° angle.

*Calyx*.—Campanulate, about 1 cm in length and 5 mm in diameter, persistent.

*Sepals*.—5, fused with the exception of apex of each, free portion is triangular in shape 5 mm in width and 3 mm in depth with an acute apex, 138B in color, surface is glabrous and satiny on both surfaces.

*Corolla features*.—Papilionaceous (4 segments) with a reflexed banner, 2 lateral wings and a concealed keel, lateral wings; oblong in shape, about 2 cm in length and 9 mm in width, color on inner surface and outer surface when opening; a mix of 157D and 4D, color on inner and outer surface when fully mature; a blend between 85B to 85D and 93B to 93C, rounded apex, oblique base, keel; not visible, comprised of 2 segments surrounding reproductive organs, oblong (slightly oblique) in shape with rounded apex and oblique base, 1.5 cm in length and 8 mm in width, upper surface and lower surface are a blend of 4D and 145D in color, segments joined at center point, banner; orbicular and strongly reflexed in shape, about 1.8 cm in length and 2 cm in width, color on upper and lower surface when opening; a blend of 157D and 4D, color on upper and lower surface when fully mature; a blend of 85B to 85D and 93B to 93C, apex is rounded with a single notch, surface is glabrous on all sections on both surfaces, lateral wings and banner fades to 91A before dropping.

*Receptacle*.—Disk-shaped, gelatinous, 137A in color, about 3 mm in diameter and 1.5 mm in depth.

Reproductive organs:

*Gynoecium*.—1 Pistil, about 2.2 cm in length, 1 mm in width; style is 145B in color and 1 cm in length; stigma minute, too small to read color, ovary is superior with a stipe, 144A in color, 1 cm in length and 2 mm in width; stipe is 145B in color, 4 mm in length and 1.5 mm in width.

*Androcoecium*.—10 stamens, not united, 2.5 cm in length and 1 mm in width; filament is 1.8 cm in length, 1 mm in width and 145D in color; anther is dorsifixed, 1.5 mm in length and 1 mm in width and 165B in color, pollen is moderate in quantity and 14B in color.

*Fruit*.—An inflated pod, technically a legume, average of 6 produced per inflorescence (open-pollinated), elliptic-oblong in shape, average of 3 cm in length by 1.5 cm in width with a beak approx. 1 cm in length, color of outer surface when mature is a blend of 202A and 201A, color of inner surface 199B, walls 1.5 mm and hard at maturity, seed; average of 5 per fruit (open-pollinated), N199B in color, oval with the hilum side more or less straight, seed compressed to flattish, 4 mm in length, 3 mm in width and 2 mm in thickness.

It is claimed:

1. A new and distinct cultivar of *Baptisia* plant named 'Lunar Eclipse' as herein illustrated and described.

* * * * *